United States Patent [19]

Kelly et al.

[11] Patent Number: 5,484,551

[45] Date of Patent: Jan. 16, 1996

[54] SUBSTITUTED PHENYL 4-[(E)-ALK-2-ENOYLOXY]BENZOATES

[75] Inventors: Stephen Kelly, Möhlin; Martin Schadt, Seltisberg, both of Switzerland

[73] Assignee: Hoffmann-La Roche Inc., Nutley, N.J.

[21] Appl. No.: 439,618

[22] Filed: May 12, 1995

[30] Foreign Application Priority Data

Jun. 29, 1994 [CH] Switzerland ............... 2067/94

[51] Int. Cl.⁶ .............. C09K 19/20; C07C 255/00; C07C 69/76; C07C 25/13
[52] U.S. Cl. ............ 252/299.67; 558/415; 560/61; 560/85; 570/127
[58] Field of Search .............. 252/299.67, 299.01; 558/415; 560/61, 85; 570/127

[56] References Cited

U.S. PATENT DOCUMENTS

| | | | |
|---|---|---|---|
| 4,683,079 | 7/1987 | Bezborodov et al. | 252/299.67 |
| 5,326,497 | 7/1994 | Buchecker et al. | 252/299.61 |
| 5,326,498 | 7/1994 | Kelly | 252/299.61 |

OTHER PUBLICATIONS

Helv. Chim. Acta, 67, 1572 (1984).

*Primary Examiner*—Shean Wu
*Attorney, Agent, or Firm*—George M. Gould; George W. Johnston; Robert A. Silverman

[57] ABSTRACT

Compounds containing a 4-[(E)-alk-2-enoyloxy]benzoate group and liquid crystalline mixtures which contain such compounds and the use of such compounds and, respectively, mixtures in electro-optical indicating devices.

The compounds are of the formula

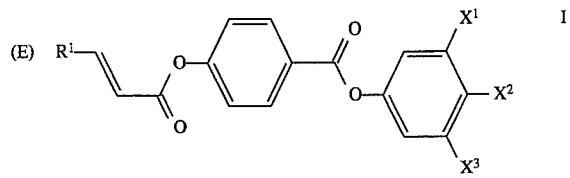

wherein
$R^1$ is alkyl with 1 to 12 carbon atoms;
$X^1$, $X^3$ each independently are halogen or hydrogen; and
$X^2$ is halogen or cyano.

20 Claims, No Drawings

SUBSTITUTED PHENYL 4-[(E)-ALK-2-ENOYLOXY] BENZOATES

BACKGROUND OF THE INVENTION

1. Field

Compounds containing a 4-[(E)-alk-2-enoyloxy]benzoate group, liquid crystalline mixtures which contain such compounds, the use of such compounds and, respectively, mixtures in electro-optical indicating devices.

2. Background

Liquid crystals are used primarily as dielectrics in indicating devices, since the optical properties of such substances can be influenced by an applied voltage. Electro-optical devices based on liquid crystals are well-known to a person skilled in the art and can be based on various effects. Such devices are, for example, cells having dynamic scattering, DAP cells (deformation of aligned phases), guest/host cells, TN cells ("twisted nematic") having a twisted nematic structure, STN cells ("super twisted nematic"), SBE cells ("super birefringence effect") and OMI cells ("optical mode interference"). The most common indicating devices are based on the Schadt-Helfrich effect and have a twisted nematic structure.

The liquid crystal materials should have a good chemical and thermal stability and, moreover, should be stable towards electric fields and electromagnetic radiation. At usual operating temperatures they should have a suitable mesophase, for example a nematic, cholesteric or tilted smectic phase. Further, the liquid crystal materials should have a low viscosity and in the cells should give short response times, low threshold potentials ($V_{10}$) and a high contrast.

Further properties such as the electrical conductivity, the dielectric anisotropy and the optical anisotropy must fulfill different requirements depending on the type of cell and field of application. For example, materials for cells having a twisted nematic structure should have a positive dielectric anisotropy and an electrical conductivity which is as low as possible. In addition to the general interest in liquid crystal materials having a low dielectric anisotropy, there has, however, recently been an increased interest in materials having a very high dielectric anisotropy and at the same time a high clearing point, especially for TN cells having a low threshold potential, for example, in the case of TN applications for so-called outdoor uses.

Since liquid crystals are usually used as mixtures of several components in order to optimize the properties, it is important that the components have a good miscibility with one another. Components which severely lower the threshold potential in mixtures even in low concentrations usually have the disadvantage that they severely lower the clearing point and significantly increase the viscosity. The problem is therefore to look for compounds having a sufficiently great influence on the threshold potential ($V_{10}$) such that they can be used in concentrations in which neither an undesired lowering of the clearing point nor an undesired high viscosity occurs.

BRIEF SUMMARY OF THE INVENTION

The present invention relates to a compound of the formula

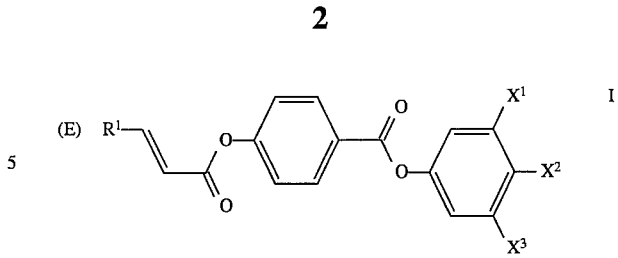

wherein $R^1$ is alkyl with 1 to 12 carbon atoms;

$X^1$, $X^3$ each independently is halogen or hydrogen; and $X^2$ is halogen or cyano.

It has been found that the introduction of an (E)-alk-2-enoyl group into known 4-cyano-3-fluorophenyl 4-alkylbenzoates (Helv. Chim. Acta, 67, 1572, 1984) favorably influences the tendency to form liquid crystal phases, above all the tendency to form a nematic phase, and to increase dielectric anisotropy. In nematic mixtures these esters lead to high clearing points and to surprisingly short switching times. The dielectric anisotropy (De) and the optical anisotropy (Dn) are surprisingly large. The threshold potential ($V_{10}$) is significantly lowered by the addition of a compound of formula I to liquid crystal mixtures.

DETAILED DESCRIPTION OF THE INVENTION

The present invention relates to a compound of the formula

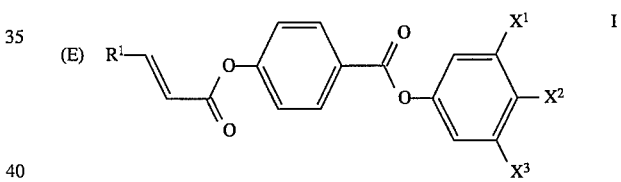

wherein $R^1$ is alkyl with 1 to 12 carbon atoms;

$X^1$, $X^3$ each independently is halogen or hydrogen; and $X^2$ is halogen or cyano.

Preferred residues $R^1$ are alkyl residues with 1 to 12 carbon atoms, such as, for example, methyl, ethyl, propyl, butyl, pentyl, hexyl, heptyl, octyl or nonyl and the like. Alkyl residues with 1 to 7, especially with 1 to 3, carbon atoms are particularly preferred.

The term "halogen" denotes fluorine, chlorine, bromine and iodine, but especially chlorine and fluorine.

"(E)" indicates the preferred configuration, as opposed to "(Z)".

Preferred compounds of formula I are those compounds in which $X^1$ is fluorine, $X^2$ is chlorine, fluorine or cyano and $X^3$ is hydrogen or fluorine, especially the compounds of the general formulae

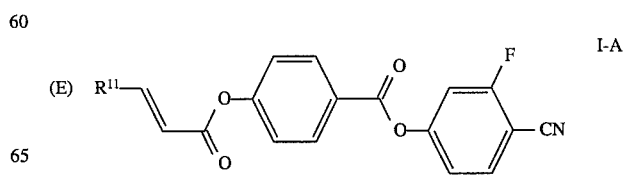

-continued

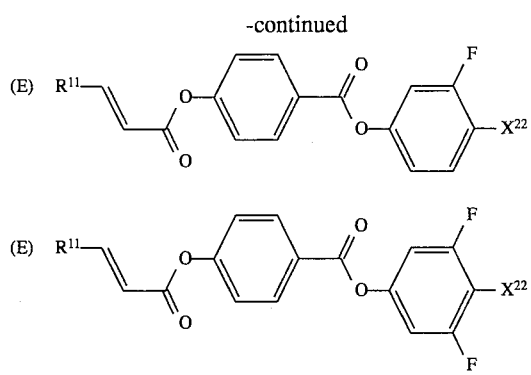

wherein 'R$^{11}$ is alkyl with 1 to 7 carbon atoms; and X$^{22}$ is fluorine or chlorine.

A preferred aspect of the invention is concerned with compounds of formulae I, I-A, 1-B and 1-C in which R$^1$ and, respectively, R$^{11}$ signify alkyl with 1 to 3 carbon atoms. A particularly preferred aspect of this invention is accordingly concerned with compounds of the formulae

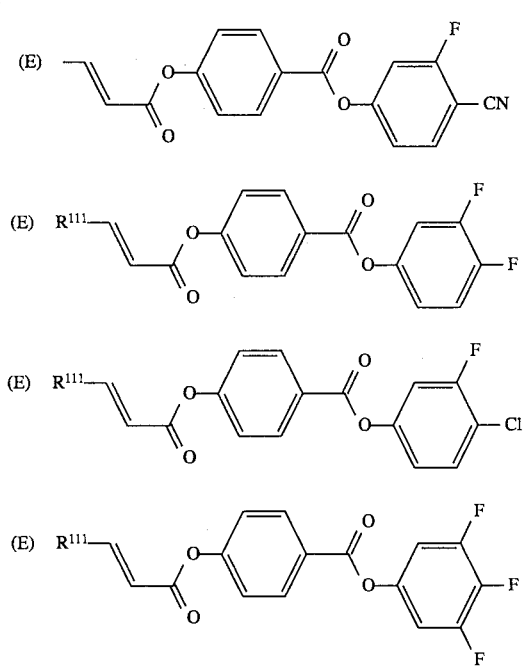

wherein R$^{111}$ is alkyl with 1 to 3 carbon atoms.

The compounds are distinguished by a surprisingly broad nematic mesophase and by a very high dielectric anisotropy (De).

By virtue of their low threshold potential and their high clearing point the compounds of formula I, especially those of formula I-A and particularly those of formula I-1, are particularly suitable for use in liquid crystal materials which are used for TN cells for outdoor applications. The present invention accordingly provides outstanding novel components for optimizing and modifying liquid crystal materials.

The compounds of general formula I in accordance with the invention can be prepared in a known manner, for example according to the method illustrated in the following Scheme and in the Examples.

SCHEME

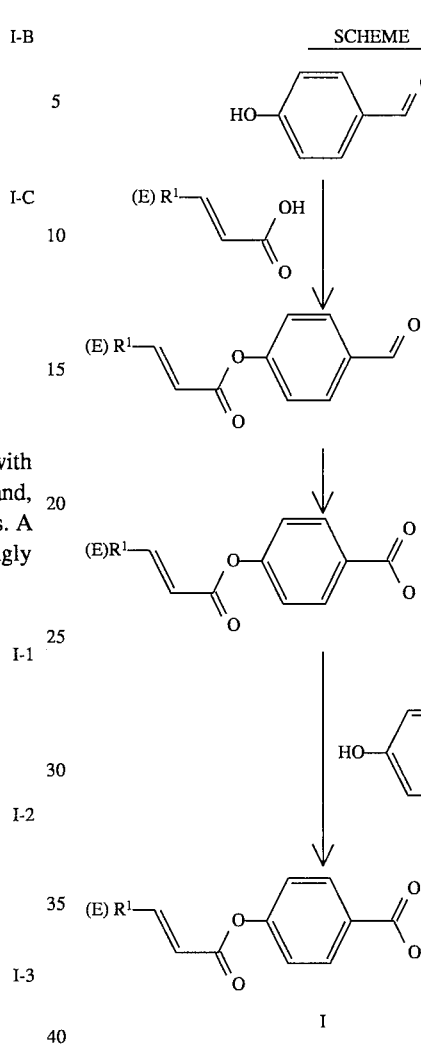

wherein R$^1$, X$^1$, X$^2$ and X$^3$ have the significances defined above.

The compounds of formula I are readily accessible synthetically and can be produced in a known manner from phenols and 4-[(E)-alk-2-enoyloxy]benzoic acids. The esterification can be effected, for example, in the presence of N,N'-dicyclohexylcarbodiimide and 4-(dimethylamino)pyridine in dichloromethane or another suitable solvent, such as e.g. chloroform. The 4-[(E)-alk-2enoyloxy]benzoic acids can be produced from the esterification product of 4-hydroxybenzaldehyde and (E)-alk-2-enoic acids by oxidation with Jones' reagent. The starting materials are known and are to some extent commercially available.

The compounds of formula I can be used in the form of mixtures with one another and/or with other liquid crystal components.

The invention is therefore also concerned with a liquid crystalline mixture having at least two components, of which at least one component is a compound of formula I. A second component and optionally additional components can be further compounds of general formula I or other suitable liquid crystal components. Suitable liquid crystal components will be known to a person skilled in the art in large numbers, for example, from D. Demus et at., Flüssige Kristalle in Tabellen, VEB Deutscher Verlag Grundstoffindustrie, Leipzig, volumes I and II, and many of them are, moreover, commercially available.

Having regard to the good solubility of the compounds of formula I in accordance with the invention in other liquid crystal materials and having regard to their good miscibility with one another, the content of compounds of formula I in the mixtures in accordance with the invention can be relatively high and can be, for example, 1–70 wt. %. In general, a content of about 3–40 wt. %, especially of about 5–20 wt./%, of compounds of formula I is preferred.

The mixtures in accordance with the invention preferably contain, in addition to one or more compounds of formula I, one or more compounds from the group of compounds of the formulae

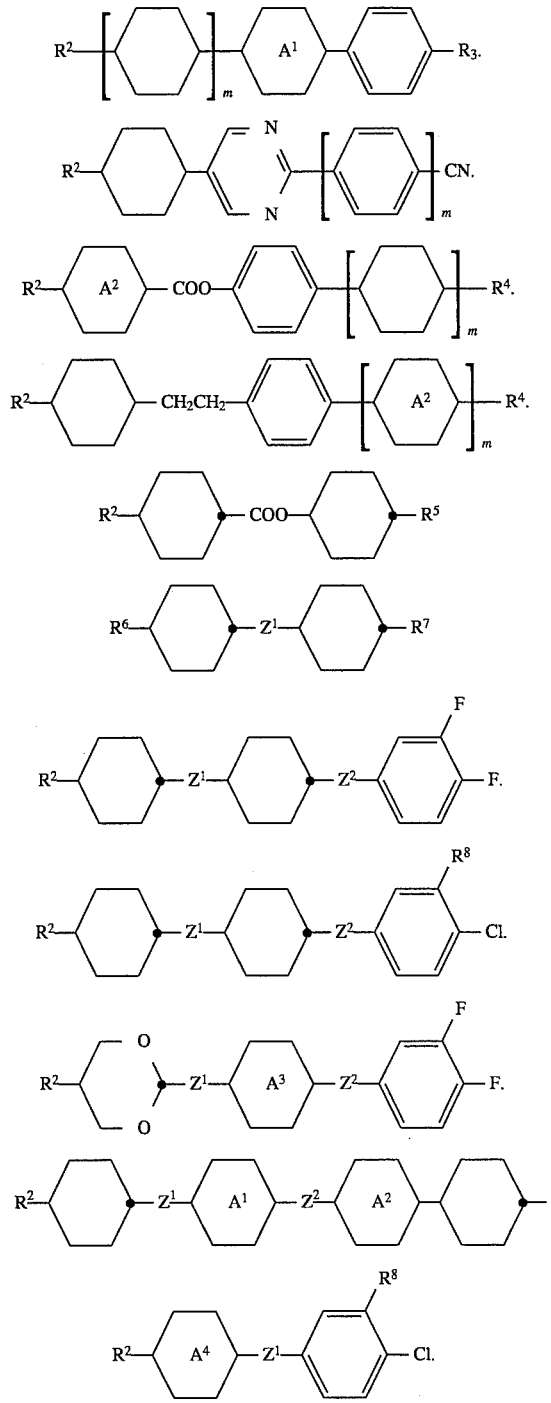

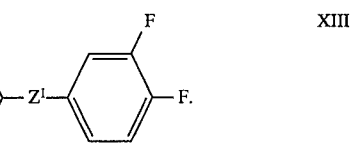

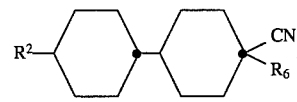

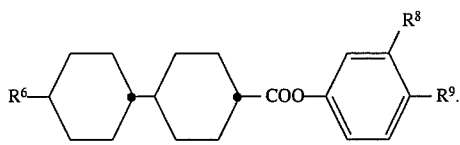

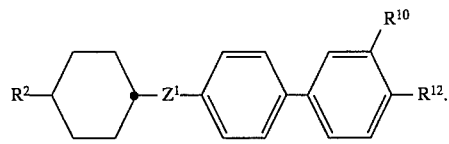

wherein
- $R^2$, $R^5$ is alkyl, alkoxyalkyl, 3E-alkenyl, 4-alkenyl or on saturated rings also 1E-alkenyl;
- m is 0 or 1;
- ring $A^1$ is 1,4-phenylene, pyridine-2,5-diyl, pyrimidine-2,5-diyl, trans-1,4-cyclohexylene or trans-1,3-dioxane-2,5-diyl;
- $R^3$ is cyano, isothiocyanato, fluorine, alkyl, 3E-alkenyl, 4-alkenyl, alkoxy, 2E-alkenyloxy, 3-alkenyloxy or 1-alkynyl;
- ring $A^2$ is 1,4-phenyene or trans-1,4-cyclohexylene;
- ring $A^3$ is 1,4-phenyene, trans-1,4-cyclohexylene or pyridine-2,5-diyl;
- ring $A^4$ is trans-1,4-cyclohexylene or trans-1,3-dioxane-2,5-diyl;
- ring $A^5$ is trans-1,4-cyclohexylene, trans-1,3-dioxane-2,5-diyl or pyrimidine-2,5-diyl;
- $R^4$ is alkyl, 3E-alkenyl, 4-alkenyl or on trans-1,4-cyclohexylene also 1E-alkenyl, or on 1,4-phenylene also cyano, isothiocyanato, alkoxy, 2E-alkenyloxy or 3-alkenyloxy;
- $R^6$ is alkyl, 1E-alkenyl, 3E-alkenyl or 4-alkenyl;
- $R^7$ is cyano, alkyl, 1E-alkenyl, 3E-alkenyl, 4-alkenyl, alkoxy, 2E-alkenyloxy, 3-alkenyloxy, alkoxymethyl or (2E-alkenyl)oxymethyl;
- $Z^1$, $Z^2$ are a single covalent bond or —$CH_2CH_2$—, with two aromatic rings always being linked by a single covalent bond;
- $R^8$ is hydrogen, fluorine or chlorine;
- $R^9$ is cyano, fluorine or chlorine,
- $R^{10}$ is hydrogen or fluorine;
- $R^{12}$ is fluorine or chlorine.

The terms used in connection with the compounds of formulae II to XVI are explained hereinafter.

"Aromatic rings" denotes rings such as, for example, 1,4-phenylene, pyridine-2,5-diyl or pyrimidine-2,5-diyl.

"Saturated rings" denotes trans-1,4-cyclohexylene or trans-1,3-dioxane-2,5-diyl.

"Alkyl" signifies preferably straight-chain groups with 1 to 12 carbon atoms, especially preferred groups have 1 to 7 carbon atoms, such as, for example, methyl, ethyl, propyl, butyl, pentyl, hexyl or heptyl.

"Alkyloxyalkyl" signifies preferably straight-chain groups, such as, for example, methoxymethyl, ethoxymethyl, propyloxymethyl, butyloxymethyl and the like.

"Alkyloxy" signifies preferably straight-chain groups, such as, for example, methoxy, ethoxy, propyloxy, butyloxy, pentyloxy, hexyloxy, heptyloxy and the like.

"1E-Alkenyl" signifies preferably straight-chain alkenyl groups in which the double bond is situated in the 1-position, such as, for example, vinyl, 1E-propenyl, 1E-butenyl, 1E-pentenyl, 1E-hexenyl, 1E-heptenyl and the like.

"3E-Alkenyl" signifies preferably straight-chain alkenyl groups in which the double bond is situated in the 3-position, such as, for example, 3-butenyl, 3E-pentenyl, 3E-hexenyl, 3E-heptenyl and the like.

"4-Alkenyl" signifies preferably straight-chain alkenyl groups in which the double bond is situated in the 4-position, such as, for example, 4-pentenyl, 4-hexenyl, 4-heptenyl and the like.

"2E-or 3-Alkenyloxy" signifies in this connection preferably straight-chain alkenyloxy groups in which the double bond is situated in the 2- or 3-position and E or Z indicates the preferred configuration, such as, for example, allyloxy, 2E-butenyloxy, 2E-pentenyloxy, 2E-hexenyloxy, 2E-heptenyloxy, 3-butenyloxy, 3-pentenyloxy, 3-hexenyoxy, 3-heptenyloxy, 4-pentenyloxy, 5-hexenyloxy, 6-heptenyloxy and the like.

"1-Alkynyl" signifies in this connection preferably straight-chain alkynyl residues in which the triple bond is situated in the 1-position, such as, for example, ethynyl, 1-propynyl, 1-butynyl, 1-pentynyl and the like.

The mixtures in accordance with the invention can also contain optically active compounds (for example, optically active 4'-alkyl or 4'-alkoxy-4-biphenylcarbonitriles) and/or dichroic coloring substances (for example, azo, azoxy or anthraquinone coloring substances). The content of such compounds is determined by the solubility, the desired pitch, color, extinction and the like. In general, the content of optically active compounds and dichroic coloring substances is a maximum of in each case about 10 wt. % in the total mixture.

The production of the mixtures in accordance with the invention and the production of the electro-optical indicating devices can be effected in a known manner.

The production of the compounds of formula I and of liquid crystalline mixtures containing these compounds is illustrated in more detail by the following Examples. C signifies a crystalline phase, S signifies a smectic phase, N signifies a nematic phase and I signifies the isotropic phrase. $V_{10}$ denotes the voltage for 10% transmission (direction of viewing perpendicular to the plate surface) $t_{on}$ and $t_{off}$ denote the switching-on time and, respectively, the switching-off time and Dn denotes the optical anisotropy.

Unless otherwise indicated (such as by the use of present tense), the following examples were carried out as stated.

DESCRIPTION OF THE PREFERRED EMBODIMENTS

EXAMPLE 1

2.6 g of N,N'-dicyclohexylcarbodiimide were added while stirring within 5 minutes to a solution of 1.2 g of 4-cyano-3-fluorophenol, 1.2 g of 4-[(E)-but-2-enoyloxy]benzoic acid and 0.1 g of 4-(dimethylamino)pyridine in 50 ml of dichloromethane. The reaction mixture was stirred overnight, then filtered. The filtrate was washed with saturated sodium bicarbonate solution and with water and concentrated. Chromatographic purification of the residue on silica gel with hexane/ethyl acetate (vol. 9:1) and two-fold recrystallization of the fractions which were pure according to thin-layer chromatography gave 2.0 g of 4-cyano-3-fluorophenyl 4-[(E)-but-2-enoyloxy]benzoate. M.p. (C-N) 125° C. and cl.p. (N-I) 195° C.

The 4-[(E)-but-2-enoyloxy]benzoic acid used as the starting material was prepared as follows:

a) 17.8 g of N,N'-dicyclohexylcarbodiimide were added while stirring within 5 minutes to a solution of 7.0 g of 4-hydroxybenzaldehyde, 7.4 g of (E)-but-2-enoic acid and 0.1 g of 4-(dimethylamino)pyridine in 50 ml of dichloromethane. The reaction mixture was stirred overnight, then filtered. The filtrate was washed with saturated sodium bicarbonate solution and with water and concentrated. Chomatographic purification of the residue on silica gel with hexane/ethyl acetate (vol. 3:7) and two-fold recrystallization of the fractions which were pure according to thin-layer chromatography gave 12.2 g of 4-[(E)-but-2-enoyloxy]benzaldehyde.

b) 50 ml of Jones' reagent were added dropwise while stirring within 15 minutes to a solution of 12.2 g of 4-[(E)-but-2-enoyloxy]benzaldehyde and 100 ml of acetone at 0° C. The reaction mixture was stirred at room temperature overnight, poured into water and extracted three times with 50 ml of ethyl acetate each time. The combined organic phases were extracted twice with 50 ml of 2N sodium hydroxide solution. The combined sodium hydroxide phases were acidified (pH 1) with hydrochloric acid, then extracted three times with SO ml of ethyl acetate. The organic phases were combined and washed twice with 50 ml of water, dried over magnesium sulphate, filtered and subsequently concentrated. Recrystallization of the residue from ethanol gave 10.5 g of 4-[(E)-but-2-enoyloxy]benzoic acid.

The following compounds were produced in an analogous manner:

4-Cyano-3-fluorophenyl 4-[(E)-pent-2-enoyloxy]benzoate, m.p. (C-N) 84° C., cl.p. (N-I) 120° C.

4-cyano-3-fluorophenyl 4-[(E)-hex-2-enoyloxy]benzoate, m.p. (C-N) 72° C., cl.p. (N-I) 119° C.

4-cyano-3-fluorophenyl 4-[(E)-hept-2-enoyloxy]benzoate, m.p. (C-N) 68° C., cl.p. (N-I) 109° C.

4-cyano-3-fluorophenyl 4-[(E)-oct-2-enoyloxy]benzoate, m.p. (C-N) 60° C., cl.p. (N-I) 110° C.

The following compounds can be produced in an analogous manner.

4-cyano-3-fluorophenyl 4-[(E)-non-2-enoyloxy]benzoate
4-cyano-3-fluorophenyl 4-[(E)-dec-2-enoyloxy]benzoate
4-cyano-3-fluorophenyl 4-[(E)-undec-2-enoyloxy]benzoate
4-cyano-3-fluorophenyl 4-[(E) -dodec-2-enoyloxy]benzoate
4-chloro-3-fluorophenyl 4-[(E)-but-2-enoyloxy]benzoate
4-chloro-3-fluorophenyl 4-[(E)-pent-2-enoyloxy]benzoate
4-chloro-3-fluorophenyl 4-[(E)-hex-2-enoyloxy]benzoate
4-chloro-3-fluorophenyl 4-[(E)-hept-2-enoyloxy]benzoate
4-chloro-3-fluorophenyl 4-[(E)-oct-2-enoyloxy]benzoate
4-chloro-3-fluorophenyl 4-[(E)-non-2-enoyloxy]benzoate
4-chloro-3-fluorophenyl 4-[(E)-dec-2-enoyloxy]benzoate
4-chloro-3-fluorophenyl 4-[(E) -undec-2-enoyloxy]benzoate
4-chloro-3-fluorophenyl 4-[(E)-dodec-2-enoyloxy]benzoate
3,4-difluorophenyl 4-[(E)-but-2-enoyloxy]benzoate 3,4-difluorophenyl 4-[(E)-pent-2-enoyloxy]benzoate
3,4-difluorophenyl 4-[(E)-hex-2-enoyloxy]benzoate
3,4-difluorophenyl 4-[(E)-hept-2-enoyloxy]benzoate
3,4-difluorophenyl 4-[(E)-oct-2-enoyloxy]benzoate
3,4-difluorophenyl 4-[(E)-non-2-enoyloxy]benzoate
3,4-difluorophenyl 4-[(E)-dec-2-enoyloxy]benzoate
3,4-difluorophenyl 4-[(E)-undec-2-enoyloxy]benzoate
3,4-difluorophenyl 4-[(E)-dodec-2-enoyloxy]benzoate
3,4,5-trifluorophenyl 4-[(E)-but-2-enoyloxy]benzoate
3,4,5-trifluorophenyl 4-[(E)-pent-2-enoyloxy]benzoate
3,4,5-trifluorophenyl 4-[(E)-hex-2-enoyloxy]benzoate
3,4,5-trifluorophenyl 4-[(E) -hept-2-enoyloxy]benzoate
3,4,5-trifluorophenyl 4-[(E)-oct-2-enoyloxy]benzoate
3,4,5-trifluorophenyl 4-[(E)-non-2-enoyloxy]benzoate
3,4,5-trifluorpohenyl 4-[(E)-dec-2-enoyloxy]benzoate
3,4,5-trifluorophenyl 4-[(E)-undec-2-enoyloxy]benzoate
3,4,5-trifluorophenyl 4-[(E) -dodec-2-enoyloxy]benzoate

EXAMPLE 2

Binary mixtures (BM) with 4-(trans-4-pentylcyclohexyl-)benzonitrile were prepared in order to investigate the properties of the compounds of formula I in mixtures. The threshold potential was measured at 22° C. in a TN cell (low bias flit) having a plate separation of 8 mm; the 2.5-fold value of the threshold potential ($V_{10}$) was chosen as the operating voltage. The clearing point [cl.p. (N-I)], the threshold potential ($V_{10}$), the switching-on time ($t_{on}$), the switching-off time ($t_{off}$) as well as the optical anisotropy (Dn) were measured. The corresponding data for 4-(trans-4-pentylcyclohexyl)benzonitrile are: cl.p. (N-I) 54.6° C., $V_{10}$=1.62 V, $t_{on}$=22 ms, $t_{off}$=40 ms and Dn=0.120.

BM-1

90 wt. % of 4-(trans-4-pentylcyclohexyl)benzonitrile 10 wt. % of 4-cyano-3-fluorophenyl 4-[(E)-but-2 enoyloxy] benzoate. cl.p. (N-I)=61.5° C., $V_{10}$=1.37 V, $T_{on}$=31 ms, $T_{off}$=51 ms, Dn=0.129.

BM-2

80 wt. % of 4-(trans-4-pentylcyclohexyl)benzonitrile 20 wt. % of 4-cyano-3-fluorophenyl 4-[(E)-but-2-enoyloxy] benzoate. cl.p. (N-I)=69.6° C., $V_{10}$=1,20 V, $T_{on}$=43 ms, $T_{off}$=70 ms, Dn=0.136.

We claim:
1. A compound of the formula

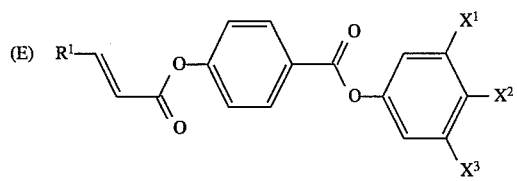

wherein
$R^1$ is alkyl with 1 to 12 carbon atoms;
$X^1$, $X^3$ each independently is halogen or hydrogen; and
$X^2$ is halogen or cyano.
2. A compound in accordance with claim 1, wherein $R^1$ is alkyl with 1 to 7 carbon atoms.
3. A compound in accordance with claim 2, wherein $R^1$ is alkyl with 1 to 3 carbon atoms.
4. A compound in accordance with claim 1, wherein $X^1$ is fluorine, $X^2$ is chlorine, fluorine or cyano and $X^3$ is hydrogen or fluorine.

5. A compound in accordance with claim 4 of the formula

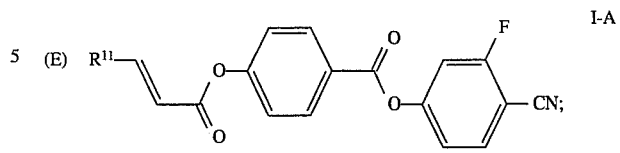

wherein
$R^{11}$ is alkyl with 1 to 7 carbon atoms.
6. A compound in accordance with claim 5, wherein $R^{11}$ is an alkyl group with 1 to 3 carbon atoms.
7. A compound in accordance with claim 4 of the formula

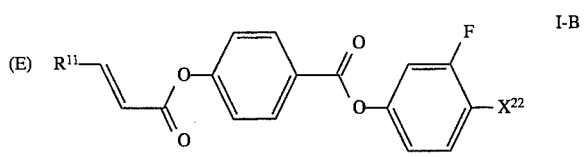

wherein
$R^{11}$ is alkyl with 1 to 7 carbon atoms; and
$X^{22}$ is fluorine or chlorine.
8. A compound in accordance with claim 7, wherein $R^{11}$ is an alkyl group with 1 to 3 carbon atoms.
9. A compound in accordance with claim 4 of the formula

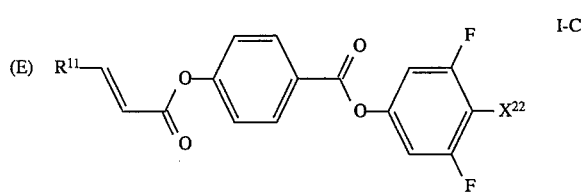

wherein
$R^{11}$ is alkyl with 1 to 7 carbon atoms; and
$X^{22}$ is fluorine or chlorine.
10. A compound in accordance with claim 9, wherein $R^{11}$ is an alkyl group with 1 to 3 carbon atoms.
11. A compound according to claim 1, 4-cyano-3-fluorophenyl 4-[(E)-but-2-enoyl-oxy]benzoate.
12. A compound according to claim 1 of the formula

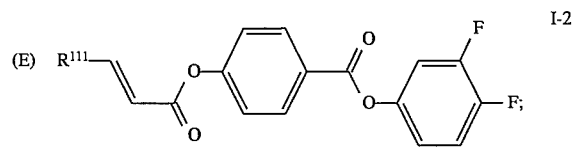

wherein $R^{111}$ is alkyl with 1 to 3 carbon atoms.
13. A compound according to claim 1 of the formula

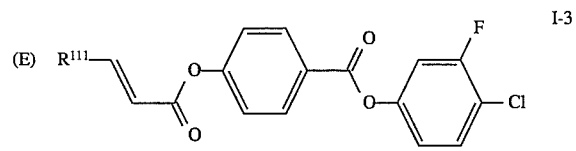

wherein $R^{111}$ is alkyl with 1 to 3 carbon atoms.
14. A compound according to claim 1 of the formula

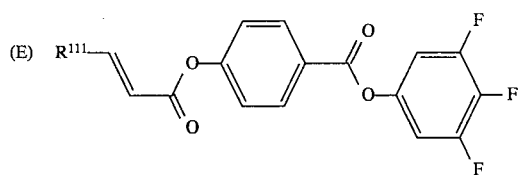

wherein R¹¹¹ is alkyl with 1 to 3 carbon atoms.

15. A liquid crystalline mixture comprising at least two components, wherein at least one component is a compound of the formula

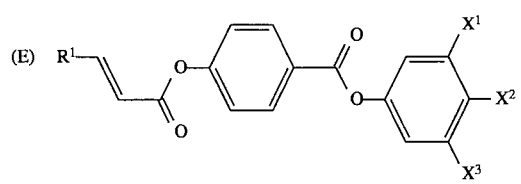

wherein $R^1$ is alkyl with 1 to 12 carbon atoms;

$X^1$, $X^3$ each independently is halogen or hydrogen; and $X^2$ is halogen or cyano.

16. A liquid crystalline mixture according to claim 15, wherein $X^1$ is fluorine, $X^2$ is chlorine, fluorine or cyano and $X^3$ is hydrogen or fluorine.

17. A liquid crystalline mixture according to claim 16, wherein $R^1$ is an alkyl group with 1 to 3 carbon atoms.

18. A liquid crystalline mixture according to claim 15, wherein the content of compounds of formula I in the mixture is 1–70 wt. %.

19. A liquid crystalline mixture according to claim 18, wherein the content of compounds of formula I in the mixture is about 3–40 wt. %.

20. A liquid crystalline mixture according to claim 19, wherein the content of compounds of formula I in the mixture is about 5–20 wt. %.

* * * * *